United States Patent
Shin et al.

(10) Patent No.: US 11,214,808 B2
(45) Date of Patent: Jan. 4, 2022

(54) METHOD OF PRODUCING 2'-FUCOSYLLACTOSE USING FUCOSYLTRANSFERASE DERIVED FROM PSEUDOPEDOBACTER SALTANS

(71) Applicant: Advanced Protein Technologies Corp., Suwon-si (KR)

(72) Inventors: Chul Soo Shin, Suwon-si (KR); Jong Won Yoon, Seongnam-si (KR); Young Ha Song, Yongin-si (KR); Young Sun You, Bucheon-si (KR); Bo Mee Kim, Suwon-si (KR); Jin Kyung Kim, Hwaseong-si (KR); Ga Eun Lee, Uiwang-si (KR)

(73) Assignee: ADVANCED PROTEIN TECHNOLOGIES CORP., Suwon-si (KR)

( * ) Notice: Subject to any disclaimer, the term of this patent is extended or adjusted under 35 U.S.C. 154(b) by 264 days.

(21) Appl. No.: 16/613,663

(22) PCT Filed: Feb. 14, 2019

(86) PCT No.: PCT/KR2019/001837
§ 371 (c)(1),
(2) Date: Nov. 14, 2019

(87) PCT Pub. No.: WO2019/194410
PCT Pub. Date: Oct. 10, 2019

(65) Prior Publication Data
US 2021/0163965 A1 Jun. 3, 2021

(30) Foreign Application Priority Data

Apr. 4, 2018 (KR) .................. 10-2018-0039121
Feb. 14, 2019 (KR) .................. 10-2019-0017144

(51) Int. Cl.
*C12N 15/77* (2006.01)
*C12P 19/18* (2006.01)
*C12P 19/24* (2006.01)

(52) U.S. Cl.
CPC ............. *C12N 15/77* (2013.01); *C12P 19/18* (2013.01); *C12P 19/24* (2013.01); *C12Y 204/01069* (2013.01); *C12Y 207/07013* (2013.01); *C12Y 504/02008* (2013.01)

(58) Field of Classification Search
CPC .............................................. C12Y 204/01069
See application file for complete search history.

(56) References Cited

U.S. PATENT DOCUMENTS

2018/0298389 A1* 10/2018 Seo .................. C12P 19/00

FOREIGN PATENT DOCUMENTS

| KR | 10-1544184 B1 | 8/2015 |
| KR | 10-1648342 B1 | 8/2016 |
| KR | 10-1648352 B1 | 8/2016 |
| KR | 10-1731263 B1 | 5/2017 |

OTHER PUBLICATIONS

Chin et al., "Enhanced production of 2'-fucosyllactose in engineered *Escherichia coli* BL21star(DE3) by modulation of lactose metabolism and fucosyltransferase", Journal of Biotechnology, 2015, vol. 210, pp. 107-115.
Chin et al., "Metabolic engineering of Corynebacterium glutamicum to produce GDP-L-fucose from glucose and mannose", Bioprocess Biosyst Eng, 2013, vol. 36, pp. 749-756.
NCBI, GenBank accession No. WP_013633823.1, "hypothetical protein [Pseudopedobacter saltans]" 1 page, 2013.
NCBI, GenBank accession No. CP002545.1, "Pseudopedobacter saltans DSM 12145 chromosome, complete genome" 973 pages, 2017.
Haynes et al., "Electrotransformation of Brevibacterium lactofermentum and Corynebacterium glutamicum: growth in tween 80 increases transformation frequencies", FEMS Microbiology Letters, vol. 61, pp. 329-334, (1989).

* cited by examiner

*Primary Examiner* — Robert J Yamasaki
*Assistant Examiner* — Charles Zoltan Constantine
(74) *Attorney, Agent, or Firm* — Sughrue Mion, PLLC

(57) ABSTRACT

Disclosed is a method for producing 2'-fucosyllactose from a recombinant *Corynebacterium* sp. introduced with fucosyltransferase derived from *Pseudopedobacter saltans*. The recombinant *Corynebacterium* sp. microorganism introduced with fucosyltransferase derived from *Pseudopedobacter saltans* is capable of producing 2'-fucosyllactose at a high concentration, high yield and high productivity.

6 Claims, 5 Drawing Sheets
Specification includes a Sequence Listing.

SEQUENCE LISTING

<160> NUMBER OF SEQ ID NOS: 7

<210> SEQ ID NO 1
<211> LENGTH: 1122
<212> TYPE: DNA
<213> ORGANISM: Escherichia coli

<400> SEQUENCE: 1

```
atgtcaaaag tcgctctcat caccggtgta accggacaag acggttctta cctggcagag      60
tttctgctgg aaaaaggtta cgaggtgcat ggtattaagc gtcgcgcatc gtcattcaac     120
accgagcgcg tggatcacat ttatcaggat ccgcacacct gcaacccgaa attccatctg     180
cattatggcg acctgagtga tacctctaac ctgacgcgca ttttgcgtga agtacagccg     240
gatgaagtgt acaacctggg cgcaatgagc cacgttgcgg tctcttttga gtcaccagaa     300
tataccgctg acgtcgacgc gatgggtacg ctgcgcctgc tggaggcgat ccgcttcctc     360
ggtctggaaa agaaaactcg tttctatcag gcttccacct ctgaactgta tggtctggtg     420
caggaaattc cgcagaaaga gaccacgccg ttctaccgcg gatctccgta tgcggtcgcc     480
aaactgtacg cctactggat caccgttaac taccgtgaat cctacggcat gtacgcctgt     540
aacggaattc tcttcaacca tgaatccccg cgccgcggcg aaaccttcgt tacccgcaaa     600
atcacccgcg caatcgccaa catcgcccag gggctggagt cgtgcctgta cctcggcaat     660
atggattccc tgcgtgactg gggccacgcc aaagactacg taaaaatgca gtggatgatg     720
ctgcagcagg aacagccgga agatttcgtt atcgcgaccg gcgttcagta ctccgtgcgt     780
cagttcgtgg aaatggcggc agcacagctg ggcatcaaac tgcgctttga aggcacgggc     840
gttgaagaga agggcattgt ggtttccgtc accgggcatg acgcgccggg cgttaaaccg     900
ggtgatgtga ttatcgctgt tgacccgcgt tacttccgtc cggctgaagt tgaaacgctg     960
ctcggcgacc cgaccaaagc gcacgaaaaa ctgggctgga accggaaat cacccctcaga    1020 gagatggtgt ctgaaatggt ggctaatgac ctcgaagcgg cgaaaaaaca ctctctgctg    1080
aaatctcacg gctacgacgt ggcgatcgcg ctggagtcat aa                       1122
```

<210> SEQ ID NO 2
<211> LENGTH: 966
<212> TYPE: DNA
<213> ORGANISM: Escherichia coli

<400> SEQUENCE: 2

```
atgagtaaac aacgagtttt tattgctggt catcgcggga tggtcggttc cgccatcagg      60
cggcagctcg aacagcgcgg tgatgtggaa ctggtattac gcacccgcga cgagctgaac     120
ctgctggaca gccgcgccgt gcatgatttc tttgccagcg aacgtattga ccaggtctat     180
ctggcggcgg cgaaagtggg cggcattgtt gccaacaaca cctatccggc ggatttcatc     240
taccagaaca tgatgattga gagcaacatc attcacgccg cgcatcagaa cgacgtgaac     300
```

| | |
|---|---:|
| aaactgctgt ttctcggatc gtcctgcatc tacccgaaac tggcaaaaca gccgatggca | 360 |
| gaaagcgagt tgttgcaggg cacgctggag ccgactaacg agccttatgc tattgccaaa | 420 |
| atcgccggga tcaaactgtg cgaatcatac aaccgccagt acggacgcga ttaccgctca | 480 |
| gtcatgccga ccaacctgta cgggccacac gacaacttcc acccgagtaa ttcgcatgtg | 540 |
| atcccagcat tgctgcgtcg cttccacgag gcgacggcac agaatgcgcc ggacgtggtg | 600 |
| gtatggggca gcggtacacc gatgcgcgaa tttctgcacg tcgatgatat ggcggcggcg | 660 |
| agcattcatg tcatggagct ggcgcatgaa gtctggctgg agaacaccca gccgatgttg | 720 |
| tcgcacatta acgtcggcac gggcgttgac tgcactatcc gcgagctggc gcaaaccatc | 780 |
| gccaaagtgg tgggttacaa aggccgggtg gttttttgatg ccagcaaacc ggatggcacg | 840 |
| ccgcgcaaac tgctggatgt gacgcgcctg catcagcttg gctggtatca cgaaatctca | 900 |
| ctggaagcgg ggcttgccag cacttaccag tggttccttg agaatcaaga ccgctttcgg | 960 |
| gggtaa | 966 |

<210> SEQ ID NO 3
<211> LENGTH: 1254
<212> TYPE: DNA
<213> ORGANISM: Escherichia coli

<400> SEQUENCE: 3

| | |
|---|---:|
| atgtactatt taaaaaacac aaacttttgg atgttcggtt tattcttttt cttttacttt | 60 |
| tttatcatgg gagcctactt cccgtttttc ccgatttggc tacatgacat caaccatatc | 120 |
| agcaaaagtg atacgggtat tatttttgcc gctatttctc tgttctcgct attattccaa | 180 |
| ccgctgtttg gtctgctttc tgacaaactc gggctgcgca ataccvtgct gtggattatt | 240 |
| accggcatgt tagtgatgtt tgcgccgttc tttattttta tcttcgggcc actgttacaa | 300 |
| tacaacattt tagtaggatc gattgttggt ggtatttatc taggcttttg ttttaacgcc | 360 |
| ggtgcgccag cagtagaggc atttattgag aaagtcagcc gtcgcagtaa tttcgaatttt | 420 |
| ggtcgcgcgc ggatgtttgg ctgtgttggc tgggcgctgt gtgcctcgat tgtcggcatc | 480 |
| atgttcacca tcaataatca gtttgtttttc tggctgggct ctggctgtgc actcatcctc | 540 |
| gccgttttac tcttttttcgc caaaacggat gcgccctctt ctgccacggt tgccaatgcg | 600 |
| gtaggtgcca accattcggc atttagcctt aagctggcac tggaactgtt cagacagcca | 660 |
| aaactgtggt ttttgtcact gtatgttatt ggcgtttcct gcacctacga tgttttttgac | 720 |
| caacagtttg ctaatttctt tacttcgttc tttgctaccg gtaacagggg tacgcgggta | 780 |
| tttggctacg taacgacaat gggcgaatta cttaacgcct cgattatgtt ctttgcgcca | 840 |
| ctgatcatta atcgcatcgg tgggaaaaac gccctgctgc tggctggcac tattatgtct | 900 |
| gtacgtatta ttggctcatc gttcgccacc tcagcgctgg aagtggttat tctgaaaacg | 960 |
| ctgcatatgt ttgaagtacc gttcctgctg gtgggctgct ttaaatatat taccagccag | 1020 |
| tttgaagtgc gttttttcagc gacgatttat ctggtctgtt tctgcttctt taagcaactg | 1080 |
| gcgatgattt ttatgtctgt actggcgggc aatatgtatg aaagcatcgg tttccagggc | 1140 |
| gcttatctgg tgctgggtct ggtggcgctg ggcttcaccct taatttccgt gttcacgctt | 1200 |
| agcggccccg gcccgctttc cctgctgcgt cgtcaggtga atgaagtcgc ttaa | 1254 |

<210> SEQ ID NO 4
<211> LENGTH: 807
<212> TYPE: DNA
<213> ORGANISM: Unknown

<220> FEATURE:
<223> OTHER INFORMATION: Pseudopedobacter saltans

<400> SEQUENCE: 4

```
atgatatttg taaccggata tggccagatg tgtaacaaca tccttcaatt tgggcatttc      60
tttgcttatg caaaagaaa tggtttaaaa acgttggct tacgttttg ctacaaatac       120
actttttca agattagtaa cgaaaaggc tataattggc cgacctatct ttatgcaaaa       180
tatgggcaa aaataggact tataaagtct gttgattttg acgaatcatt cgaaggtaca       240
aatgtagatt ctcttcaatt agacaaacaa accgtgttag ccaaaggctg gtatttaga       300
gactaccagg gatttcttaa ttaccgtaat gagcttaaag cacttttcga ctttaaagag       360
catattaaga aaccggtaga acagttttt tcaacgttat caaagacac catcaaagta        420
ggcctgcata taagacgtgg tgattataag acctggcacc agggtaaata cttttttagc       480
gacgaagaat acggtcaaat cgtaaattct tttgctaaaa gtttagataa accggtagaa       540
ttaattattg ttagcaatga tcccaaacta acagcaaaa gttttgaaaa tttaacatcc        600
tgtaaagtat caatgttaaa tggcaatcct gccgaagatc tttaccttct ttctaaatgt       660
gattatatta ttggccctcc cagcactttt tctttaatgg cagctttta cgaagaccgc       720
cctttatatt ggatatttga taagaaaaa cagcttttag cagaaaactt tgacaagttc       780
gagaatctgt ttcgacacat tatttaa                                          807
```

<210> SEQ ID NO 5
<211> LENGTH: 268
<212> TYPE: PRT
<213> ORGANISM: Unknown
<220> FEATURE:
<223> OTHER INFORMATION: Pseudopedobacter saltans

<400> SEQUENCE: 5

```
Met Ile Phe Val Thr Gly Tyr Gly Gln Met Cys Asn Asn Ile Leu Gln
1               5                   10                  15

Phe Gly His Phe Phe Ala Tyr Ala Lys Arg Asn Gly Leu Lys Thr Val
            20                  25                  30

Gly Leu Arg Phe Cys Tyr Lys Tyr Thr Phe Phe Lys Ile Ser Asn Glu
        35                  40                  45

Lys Gly Tyr Asn Trp Pro Thr Tyr Leu Tyr Ala Lys Tyr Gly Ala Lys
    50                  55                  60

Ile Gly Leu Ile Lys Ser Val Asp Phe Asp Glu Ser Phe Glu Gly Thr
65                  70                  75                  80

Asn Val Asp Ser Leu Gln Leu Asp Lys Gln Thr Val Leu Ala Lys Gly
                85                  90                  95

Trp Tyr Phe Arg Asp Tyr Gln Gly Phe Leu Asn Tyr Arg Asn Glu Leu
            100                 105                 110

Lys Ala Leu Phe Asp Phe Lys Glu His Ile Lys Lys Pro Val Glu Gln
        115                 120                 125

Phe Phe Ser Thr Leu Ser Lys Asp Thr Ile Lys Val Gly Leu His Ile
    130                 135                 140

Arg Arg Gly Asp Tyr Lys Thr Trp His Gln Gly Lys Tyr Phe Phe Ser
145                 150                 155                 160

Asp Glu Glu Tyr Gly Gln Ile Val Asn Ser Phe Ala Lys Ser Leu Asp
                165                 170                 175

Lys Pro Val Glu Leu Ile Ile Val Ser Asn Asp Pro Lys Leu Asn Ser
            180                 185                 190
```

```
Lys Ser Phe Glu Asn Leu Thr Ser Cys Lys Val Ser Met Leu Asn Gly
            195                 200                 205

Asn Pro Ala Glu Asp Leu Tyr Leu Leu Ser Lys Cys Asp Tyr Ile Ile
210                 215                 220

Gly Pro Pro Ser Thr Phe Ser Leu Met Ala Ala Phe Tyr Glu Asp Arg
225                 230                 235                 240

Pro Leu Tyr Trp Ile Phe Asp Lys Glu Lys Gln Leu Leu Ala Glu Asn
                245                 250                 255

Phe Asp Lys Phe Glu Asn Leu Phe Arg His Ile Ile
            260                 265
```

```
<210> SEQ ID NO 6
<211> LENGTH: 903
<212> TYPE: DNA
<213> ORGANISM: Helicobacter pylori

<400> SEQUENCE: 6
atggctttca aggtggtcca aatttgtggt ggacttggca atcagatgtt tcagtacgca      60
tttgcgaaaa gcctgcaaaa acattcgaat acgcctgtac tcctcgacat cacctcattt    120
gattggagcg atcggaaaat gcagctcgag cttttcccca ttgatctccc ctatgcgtct    180
gccaaggaga ttgccattgc gaaaatgcaa caccttccga aattggtacg tgacgcgctg    240
aaatgcatgg gattcgaccg tgtgtctcag gaaatcgtct ttgagtacga acctaagctg    300
ctgaagccat cgcgtttgac gtatttttc ggatactttc aagacccacg gtattttgac     360
gcaattagcc cacttattaa gcagacgttt actttgccac ccccaccaga aaacaacaag    420
aataacaaca gaaggagga agagtatcaa tgcaaactta gcttgatttt ggcagctaaa     480
aattcggtat tgttcatat ccgccggggt gactatgtcg gaatcggatg ccaacttgga     540
atcgactacc agaaaaaggc tcttgagtac atggctaagc gtgtccccaa tatggaactc    600
ttcgtctttt gcgaggatct ggagttcacc cagaaacctcg atctcggcta tccgttcatg   660
gacatgacca cccgcgacaa agaggaagaa gcatactggg atatgctgtt gatgcagtct    720
tgtcagcacg cgatcattgc aaattccact tactcatggt gggcggccta cctttattgaa   780
aatcctgaga aaattatcat cggaccaaag cactggctct ttggacacga aaacattctc    840
tgtaaggagt gggtgaagat cgaaagccat ttcgaagtga agagccagaa atacaatgct    900
taa                                                                  903
```

```
<210> SEQ ID NO 7
<211> LENGTH: 300
<212> TYPE: PRT
<213> ORGANISM: Helicobacter pylori

<400> SEQUENCE: 7

Met Ala Phe Lys Val Val Gln Ile Cys Gly Gly Leu Gly Asn Gln Met
1               5                   10                  15

Phe Gln Tyr Ala Phe Ala Lys Ser Leu Gln Lys His Ser Asn Thr Pro
            20                  25                  30

Val Leu Leu Asp Ile Thr Ser Phe Asp Trp Ser Asp Arg Lys Met Gln
        35                  40                  45

Leu Glu Leu Phe Pro Ile Asp Leu Pro Tyr Ala Ser Ala Lys Glu Ile
    50                  55                  60

Ala Ile Ala Lys Met Gln His Leu Pro Lys Leu Val Arg Asp Ala Leu
65                  70                  75                  80
```

```
Lys Cys Met Gly Phe Asp Arg Val Ser Gln Glu Ile Val Phe Glu Tyr
                85                  90                  95

Glu Pro Lys Leu Leu Lys Pro Ser Arg Leu Thr Tyr Phe Phe Gly Tyr
            100                 105                 110

Phe Gln Asp Pro Arg Tyr Phe Asp Ala Ile Ser Pro Leu Ile Lys Gln
        115                 120                 125

Thr Phe Thr Leu Pro Pro Pro Glu Asn Asn Lys Asn Asn Asn Lys
    130                 135                 140

Lys Glu Glu Glu Tyr Gln Cys Lys Leu Ser Leu Ile Leu Ala Ala Lys
145                 150                 155                 160

Asn Ser Val Phe Val His Ile Arg Arg Gly Asp Tyr Val Gly Ile Gly
                165                 170                 175

Cys Gln Leu Gly Ile Asp Tyr Gln Lys Lys Ala Leu Glu Tyr Met Ala
            180                 185                 190

Lys Arg Val Pro Asn Met Glu Leu Phe Val Phe Cys Glu Asp Leu Glu
            195                 200                 205

Phe Thr Gln Asn Leu Asp Leu Gly Tyr Pro Phe Met Asp Met Thr Thr
    210                 215                 220

Arg Asp Lys Glu Glu Glu Ala Tyr Trp Asp Met Leu Leu Met Gln Ser
225                 230                 235                 240

Cys Gln His Ala Ile Ile Ala Asn Ser Thr Tyr Ser Trp Trp Ala Ala
                245                 250                 255

Tyr Leu Ile Glu Asn Pro Glu Lys Ile Ile Ile Gly Pro Lys His Trp
            260                 265                 270

Leu Phe Gly His Glu Asn Ile Leu Cys Lys Glu Trp Val Lys Ile Glu
        275                 280                 285

Ser His Phe Glu Val Lys Ser Gln Lys Tyr Asn Ala
    290                 295                 300
```

METHOD OF PRODUCING 2'-FUCOSYLLACTOSE USING FUCOSYLTRANSFERASE DERIVED FROM PSEUDOPEDOBACTER SALTANS

SEQUENCE LISTING

The Sequence Listing submitted in text format (.txt) filed on Nov. 14, 2019, named "SequenceListing.txt", created on Nov. 14, 2019 (11.3 KB), is incorporated herein by reference.

TECHNICAL FIELD

The present invention relates to a method for producing 2'-fucosyllactose (2'-FL), and more particularly to a method for producing 2'-fucosyllactose from a recombinant *Corynebacterium* sp. introduced with fucosyltransferase derived from *Pseudopedobacter saltans*.

BACKGROUND ART

Human breast milk contains 200 or more kinds of human milk oligosaccharides (HMOs) having different structures which are present at a considerably higher concentration (5 to 15 g/L) than other mammals. HMOs include D-glucose (Glc), D-galactose (Gal), N-acetylglucosamine (GlcNAc), L-fucose (Fuc) and sialic acid [Sia; N-acetyl neuraminic acid (Neu5Ac)].

Since the HMOs have a very diverse and complex structure, about 200 isomers having different residues and glycosyl bonds may exist at different degrees of polymerization (DP 3-20). However, despite the structural complexity, HMOs have some common structures, most of which have lactose (Galβ1-4Glc) residues at the reducing ends. Gal of lactose is sialylated in the form of 3-sialyllactose or 6-sialyllactose through α-(2,3)- and α-(2,6)-bonds, respectively, or is fucosylated in the form of 2'-fucosyllactose (2'-FL) or 3'-fucosyllactose (3'-FL) through α-(1,2)- and α-(1,3)-bond.

137 oligosaccharides including three types of oligosaccharides that have the highest contents in mother's milk, are fucosylated, and account for about 77% and the remaining (39) oligosaccharides are mostly sialylated and account for about 28%. Of these, in particular, 2-fucosyllactose and 3-fucosyllactose are major HMOs that provide a variety of biological activities having positive effects on the development and health of infants, such as prebiotic effects that help the growth of intestinal lactic acid bacteria, prevention of pathogen infections, regulation of the immune system and brain development. For this reason, experts emphasize that breastfeeding in infancy is very important.

However, about 20% of women are known to be unable to synthesize fucosyltransferase properly due to mutations in the fucosyltransferase that synthesizes fucosyl-oligosaccharides. For this reason, the industrial production of fucosyllactose is required.

Meanwhile, methods of producing fucosyllactose include direct extraction from breast milk and chemical or enzymatic synthesis. However, direct extraction has drawbacks of limited breast milk supply and thus low productivity, and chemical synthesis has drawbacks of expensive substrates, low stereo-selectivity and production yield, the use of toxic organic solvents, and the like. In addition, enzymatic synthesis has drawbacks in that GDP-L-fucose used as a fucose donor is very expensive and purification of fucosyltransferase is also expensive.

Due to the above problems, it is difficult to apply direct extraction and chemical or enzymatic production to the mass production of fucosyllactose. Therefore, in an attempt to solve this problem, the production of 2'-fucosyllactose using microorganisms arose. Conventional methods for producing 2'-fucosyllactose using microorganisms were mostly production techniques using recombinant *E. coli*. However, *E. coli*, which is used for experiments, is strongly considered to be a harmful bacterium by consumers, although it is not actually a pathogen.

In addition, *E. coli* incurs high costs for separation and purification because the cell membrane component can act as an endotoxin. For this reason, it is difficult to use *E. coli* as a host cell to produce fucosyllactose which is a food and/or medicinal material.

DISCLOSURE

Technical Problem

Therefore, the present invention has been made in view of the above problems, and it is one object of the present invention to provide a method for producing 2'-fucosyllactose using a recombinant *Corynebacterium* sp. microorganism introduced with fucosyltransferase derived from *Pseudopedobacter saltans*, as a host cell producing fucosyllactose which is a food and/or medicinal material.

Technical Solution

In accordance with the present invention, the above and other objects can be accomplished by the provision of a recombinant *Corynebacterium* sp. microorganism, which is transformed to express α-1,2-fucosyltransferase having an amino acid sequence set forth in SEQ ID NO: 5, derived from *Pseudopedobacter saltans*, is transformed to express GDP-D-mannose-4,6-dehydratase, is transformed to express GDP-L-fucose synthase, and is transformed to express lactose permease, wherein the recombinant *Corynebacterium* sp. microorganism has phosphomannomutase and GTP-mannose-1-phosphate guanylyltransferase.

The recombinant *Corynebacterium* sp. microorganism preferably includes any one selected from *Corynebacterium glutamicum*, *Corynebacterium ammoniagenes* and *Corynebacterium thermoaminogenes*.

In the recombinant *Corynebacterium* sp. microorganism of the present invention, the α-1,2-fucosyltransferase having the amino acid sequence set forth in SEQ ID NO: 5 is preferably encoded by a nucleic acid sequence set forth in SEQ ID NO: 4.

In the recombinant *Corynebacterium* sp. microorganism of the present invention, the recombinant *Corynebacterium* sp. microorganism is preferably transformed to overexpress phosphomannomutase and is transformed to overexpress GTP-mannose-1-phosphate guanylyltransferase.

In accordance with another aspect, provided is a method of producing 2'-fucosyllactose including culturing, in a medium supplemented with lactose, the recombinant *Corynebacterium* sp. microorganism according to the present invention.

In the method of producing 2'-fucosyllactose, the medium preferably further includes glucose.

Advantageous Effects

According to the present invention, a recombinant *Corynebacterium* sp. microorganism introduced with fucosyltransferase derived from *Pseudopedobacter saltans* is capable of producing 2'-fucosyllactose at a high concentration, high yield and high productivity.

DESCRIPTION OF DRAWINGS

The above and other objects, features and other advantages of the present invention will be more clearly understood from the following detailed description taken in conjunction with the accompanying drawings, in which.

BEST MODE

Figure 1:
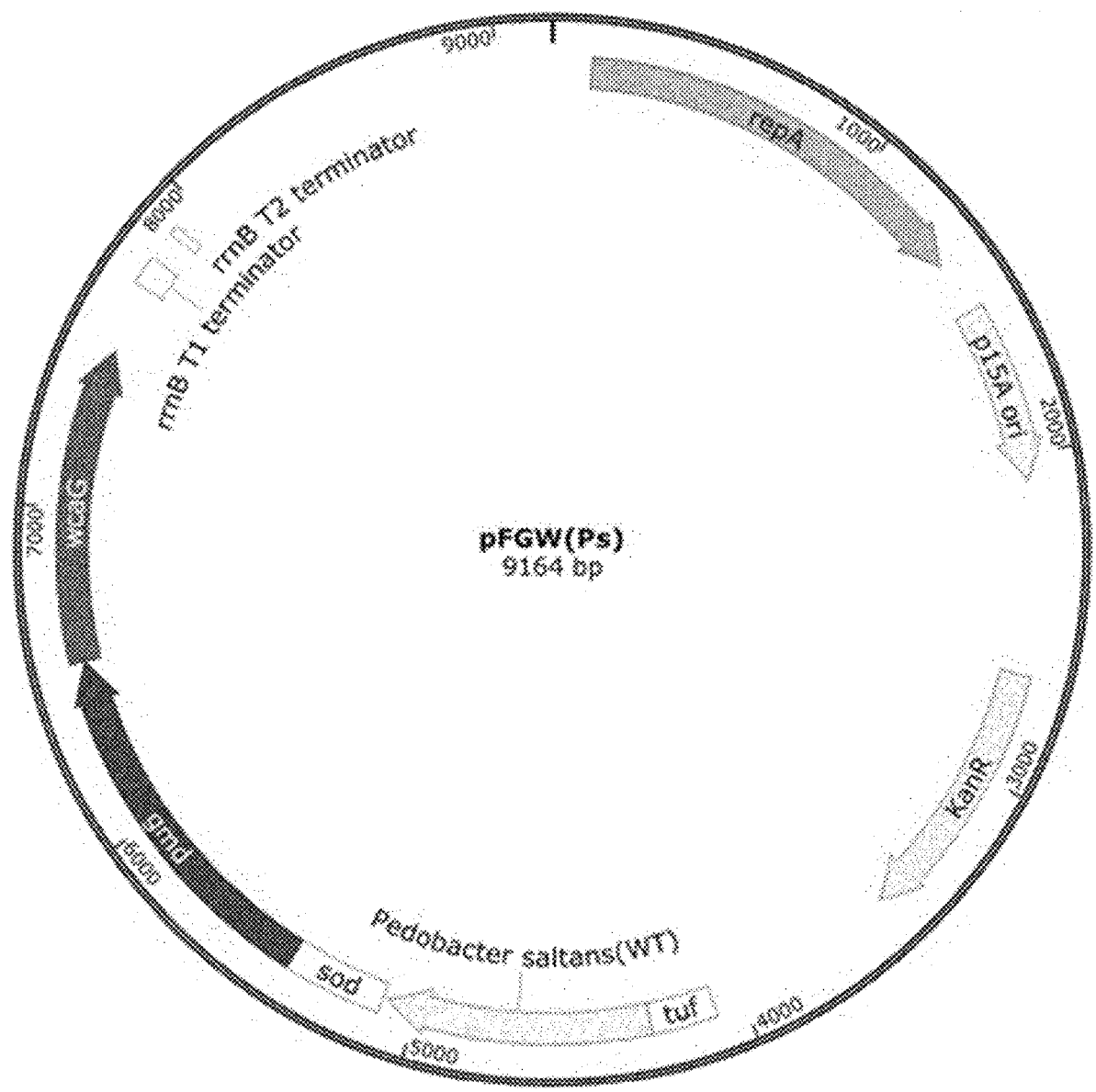
FIG. 1 is a schematic diagram showing pFGW(Ps) plasmids.

In one aspect, the present invention is directed to a recombinant *Corynebacterium* sp. microorganism, which is transformed to express α-1,2-fucosyltransferase having the amino acid sequence set forth in SEQ ID NO: 5 derived from *Pseudopedobacter saltans*, is transformed to express GDP-D-mannose-4,6-dehydratase, is transformed to express GDP-L-fucose synthase, and is transformed to express lactose permease, wherein the recombinant *Corynebacterium* sp. microorganism has phosphomannomutase and GTP-mannose-1-phosphate guanylyltransferase.

The recombinant *Corynebacterium* sp. microorganism preferably includes any one selected from *Corynebacterium glutamicum, Corynebacterium ammoniagenes* and *Corynebacterium thermoaminogenes*.

Meanwhile, since *Brevibacterium flavum* is currently classified as *Corynebacterium glutamicum, Brevibacterium flavum* strains also fall within the scope of the present invention.

In addition, since, according to the UniProt database, *Brevibacterium saccharolyticum* is used as a synonym for *Corynebacterium glutamicum*, and *Brevibacterium lactofermentum* is another name for *Corynebacterium glutamicum*, *Brevibacterium saccharolyticum* and *Brevibacterium lactofermentum* also fall within the scope of the present invention (W. LIEBL et al. INTERNATIONAL JOURNAL OF SYSTEMATIC BACTERIOLOGY, April 1991, p. 255-260; LOTHAR EGGELING et al. JOURNAL OF BIOSCIENCE AND BIOENGINEERING Vol. 92, No. 3, 201-213. 2001; Jill A. Haynes et al. FEMS Microbiology Letters 61 (1989) 329-334).

The prevent inventors obtained Korean Patent No. 10-17312630000 (Apr. 24, 2017), entitled "Method for producing 2'-fucosyllactose using *Corynebacterium*". Accordingly, in accordance with the present invention, by inserting a fucosyltransferase derived from *Pseudopedobacter saltans* into *Corynebacterium*, 2'-fucosyllactose is able to be produced in significantly higher amounts compared to 2'-fucosyllactose produced by inserting a conventional fucosyltransferase derived from *Helicobacter pylori* into *Corynebacterium*.

Meanwhile, unlike conventionally used *Escherichia coli, Corynebacterium glutamicum* or *Corynebacterium ammoniagenes* is considered to be a GRAS (generally recognized as safe) strain which does not produce endotoxins and is widely used for industrially producing amino acids and nucleic acids as food additives. Accordingly, *Corynebacterium glutamicum* or *Corynebacterium ammoniagenes* is considered to be a strain suitable for the production of food and medicinal materials while advantageously eliminating customer fears about safety.

However, since *Escherichia coli*, and *Corynebacterium* sp. microorganisms including *Corynebacterium glutamicum, Corynebacterium ammoniagenes* and *Corynebacterium thermoaminogenes* have inherently different genetic properties, strategies different from those for *Escherichia coli* should be applied to *Corynebacterium*. *Escherichia coli* and *Corynebacterium glutamicum* are the same in that external α-1,2-fucosyltransferase should be basically introduced in order to produce 2'-fucosyllactose. However, GDP-D-mannose-4,6-degydratase (Gmd), GDP-L-fucose synthase (WcaG), and lactose permease (LacY) should be further introduced into the *Corynebacterium* sp. microorganism.

At this time, in the recombinant *Corynebacterium* sp. microorganism of the present invention, α-1,2-fucosyltransferase having the amino acid sequence set forth in SEQ ID NO: 5 is preferably encoded by the nucleic acid sequence set forth in SEQ ID NO: 4, and genes encoding GDP-D-mannose-4,6-dehydratase (Gmd), GDP-L-fucose synthase, GDP-4-keto-6-deoxymannose-3,5-epimerase-4-reductase (WcaG) and lactose permease (LacY) may be conventionally known genes, and preferably, genes derived from *E. coli* are used. However, it should be noted that lactose permease (LacY) is an enzyme involved in transporting lactose present outside the strain to the inside thereof. However, since incorporating a Lac operon in the present invention aims at introducing lactose, there is no need to incorporate lacA genes, and it is sufficient simply for lacY genes to be incorporated.

Meanwhile, since the recombinant *Corynebacterium* sp. microorganism has genes encoding phosphomannomutase (ManB) and GTP-mannose-1-phosphate guanylyltransferase (ManC) and thus are capable of expressing these enzymes. For this reason, it is not necessary to overexpress these enzymes. However, it is necessary to overexpress such enzymes for mass-production. Therefore, the recombinant *Corynebacterium* sp. microorganism is preferably transformed to overexpress phosphomannomutase and is transformed to overexpress GTP-mannose-1-phosphate guanylyltransferase.

In another aspect, the present invention is directed to a method of producing 2'-fucosyllactose including culturing, in a medium supplemented with lactose, the recombinant *Corynebacterium* sp. microorganism according to the present invention. In accordance with the following experiment of the present invention, the recombinant *Corynebacterium* sp. microorganism was capable of producing 2'-fucosyllactose at a high concentration, high yield and high productivity compared to a conventional strain.

Meanwhile, regarding the method for producing 2'-fucosyllactose according to the present invention, the medium preferably further includes glucose. By adding glucose to the medium, the growth of a strain can be facilitated, and 2'-fucosyllactose can thus be produced at higher productivity.

Meanwhile, the method for producing 2'-fucosyllactose according to the present invention is preferably carried out through fed-batch culture that involves further supplying glucose or lactose. The reason for this is that continuous supply of glucose or lactose through fed-batch culture can further facilitate cell growth and produce fucosylactose at high purity, high yield and high productivity. The detailed technologies associated with fed-batch culture are well-known in the art and are not described herein.

Mode for Invention

Hereinafter, the present invention will be described in more detail with reference to the following examples, but the scope of the present invention is not limited to the examples, and includes variations and technical concepts equivalent thereto.

Meanwhile, only the effect when using *Corynebacterium glutamicum* as a host cell will be described below, but *Corynebacterium glutamicum*, *Corynebacterium ammonia genes*, *Corynebacterium thermoaminogenes*, *Brevibacterium flavum* and *Brevibacterium lactofermentum* are expected to have the same effect, because the transformation system can be equally applied thereto.

Production Example 1: Production of Recombinant Plasmids

*Escherichia coli* K-12 MG1655 and *Corynebacterium glutamicum* ATCC 13032 were used in order to produce plasmids and 2'-fucosyllactose (2'-FL), respectively.

In order to establish pFGW(Ps) plasmids, gmd-wcaG gene clusters were amplified through PCR reaction using two DNA primers, namely GW-F and GW-R, from the genomic DNAs of K-12 MG1655, *E. Coli*, the promoters of the Sod gene were amplified through PCR reaction using two DNA primers, namely Sod-F and Sod-R from the genomic DNA of *Corynebacterium glutamicum* ATCC 13032, and then PSod-Gmd-WcaG DNA fragments were synthesized through an overlapping PCR reaction using two DNA primers, namely Sod-F and GW-R.

In addition, the transcription termination sequence was amplified from the pXMJ19 plasmids through PCR reaction using two DNA primers, namely Ter-F and Ter-R, and a PSod-Gmd-WcaG-ter sequence was synthesized from the synthesized pSod-Gmd-WcaG and transcription termination sequence as templates through PCR reaction using DNA primers Sod-F and Ter-R, and was then inserted into the pCES208 plasmids cut by the restriction enzyme, BamHI, to establish pGW plasmids.

In addition, a Tuf gene promoter was amplified through PCR reaction using two DNA primers Tuf-F1 and Tuf-R1 from the genomic DNAs of *Corynebacterium glutamicum* ATCC 13032, and α-1,2-fucosyltransferase was amplified through PCR reaction using two DNA primers, FT(Ps)-F and FT(Ps)-R, from the synthesized α-1,2-fucosyltransferase derived from *Pseudopedobacter saltans* DSM 12145, and pTuf-FT (Ps) DNA fragments were synthesized through an overlapping PCR reaction using two primers Tuf-F and FT(Ps)-R. The pTuf-FT (Ps) DNA fragments were inserted into the established pGW plasmid by treating with restriction enzyme NotI to establish PFGW(Ps) plasmids.

Meanwhile, in order to establish pXIL plasmids, lacY genes were amplified through PCR reaction using two DNA primers, namely ilvC-lacY-F and lacY pX-R, from the genomic DNAs of K-12 MG1655, *E. Coli*, the promoters of the ilvC genes were amplified through PCR reaction using two DNA primers, namely pX-ilvC-F and ilvC-lacY-R, from the genomic DNA of *Corynebacterium glutamicum* ATCC 13032, and then pilvC-lacY DNA fragments were synthesized through an overlapping PCR reaction using two DNA primers, namely pX-ilvC-F and ilvC-lacY-R, and the pilvC-lacY fragments were inserted into the pX plasmid (pXMJ19) treated with restriction enzymes, Not I and EcoR I to establish pXIL plasmids.

Meanwhile, in order to establish pFGW(Hp) plasmids, the established pGW plasmids were used, and Tuf gene promoters were amplified through PCR reaction using two DNA primers, namely Tuf-F1 and Tuf-R2, from the genomic DNAs of *Corynebacterium glutamicum* ATCC 13032, α-1, 2-fucosyltransferase was amplified through PCR reaction using two DNA primers, namely FT(Hp)-F and FT(Hp)-R from the *Helicobacter pylori* ATCC 700392-derived α-1,2-fucosyltransferase synthesized through codon optimization of *Corynebacterium glutamicum*, and then pTuf-FT(Ps) DNA fragments were synthesized through an overlapping PCR reaction using two DNA primers, namely Tuf-F1 and FT(Hp)-R. Then, the pTuf-FT(Ps) DNA fragments were inserted into the established pGW plasmid by treating the established pGW plasmid with restriction enzyme NotI to establish pFGW(Hp) plasmids.

Meanwhile, the strains, plasmids and nucleic acid and amino acid sequences used for the present Production Example are shown in Tables 1 to 4 below.

TABLE 1

| Strains | |
| --- | --- |
| *E. coli* K-12 MG1655 | F⁻, lambda⁻, rph-1 |
| *C. glutamicum* | Wild-type strain, ATCC13032 |

TABLE 2

| Nucleic acid and amino acid sequences | |
| --- | --- |
| gmd nucleic acid sequence | SEQ ID NO: 1 |
| wcaG nucleic acid sequence | SEQ ID NO: 2 |
| lacY nucleic acid sequence | SEQ ID NO: 3 |
| FT(Ps) nucleic acid sequence | SEQ ID NO: 4 |
| FT(Ps) amino acid sequence | SEQ ID NO: 5 |
| FT(Hp) nucleic acid sequence | SEQ ID NO: 6 |
| FT(Hp) amino acid sequence | SEQ ID NO: 7 |

TABLE 3

| Primers | |
| --- | --- |
| primer | Sequence (5'→3') |
| pX-ilvC-F | GTCATATGATGGTCGCGGATCCGAATTCCCAGGCAAGCTCCGC |
| ilvC-lacY-R | GTTTTTTAAATAGTACATAATCTCGCCTTTCGTAAAAATTTTGGT |

TABLE 3-continued

Primers

| primer | Sequence (5'→3') |
|---|---|
| ilvC-lacY-F | TTACGAAAGGCGAGATTATGTACTATTTAAAAAACACAAACTTTTGGATGTTCGG |
| lacY pX-R | GCCTTTCGTTTTATTTGCTCGAGTGCGGCCGCTTAAGCGACTTCATTCACCTGACGAC |
| Tuf-F1 | TGGAGCTCCACCGCGGTGGCTGGCCGTTACCCTGCGAA |
| Tuf-R1 | CAAATATCATTGTATGTCCTCCTGGACTTCG |
| FT(ps)-F | AGGACATACAATGATATTTGTAACCGGATATG |
| FT(ps)-R | CGCTTCACTAGTTCTAGAGCTTAAATAATGTGTCGAAACAGATTC |
| Sod-F | GCTCTAGAACTAGTGAAGCGCCTCATCAGCG |
| Sod-R | TACACCGGTGATGAGAGCGACTTTTGACATGGTAAAAAATCCTTTCGTAGGTTTCCGCAC |
| GW-F | ATGTCAAAAGTCGCTCTCATCACCGGTGTA |
| GW-R | CAAGCTGAATTCTTACCCCCGAAAGCGGTC |
| ter-F | GACCGCTTTCGGGGGTAAGAATTCAGCTTG |
| ter-R | GGTATCGATAAGCTTGATATCGAATTCCTGCAGCCCGGGGAAAAGGCCATCCGTCAGGAT |
| Tuf-R2 | TGAAAGCCATTGTATGTCCTCCTGGACTTCGT |
| FT(Hp)-F | GGACATACAATGGCTTTCAAGGTGGTCCAAAT |
| FT(Hp)-R | GCTTCACTAGTTCTAGAGCTTAAGCATTGTATTTCTGGCTCTTCACTTCG |

TABLE 4

Plasmids

| Plasmid | Related features | Ref. |
|---|---|---|
| pCES208 | $Km^R$, *C. glutamicum/E. coli* shuttle vector | J. Microbiol. Biotechnol. (2008), 18(4), 639647 |
| pXMJ19 | $Cm^R$, *C. glutamicum/E. coli* shuttle vector | Biotechnology Techniques (1999), 13, 437441 |
| pGW | pCES208 + Sod-gmd-wcaG | Present invention |
| pFGW(Ps) | pCES208 + Tuf-FT(Ps) + Sod-gmd-wcaG | Present invention |
| pFGW(Hp) | pCES208 + Tuf-FT(Hp) + Sod-gmd-wcaG | Present invention |
| pXIL | pXMJ19 + ilvC-lacY | Present invention |

Example 1: Culture of Recombinant Strain Introduced with Fucosyltransferase Derived from *Pseudopedobacter saltans*

Figure 2:
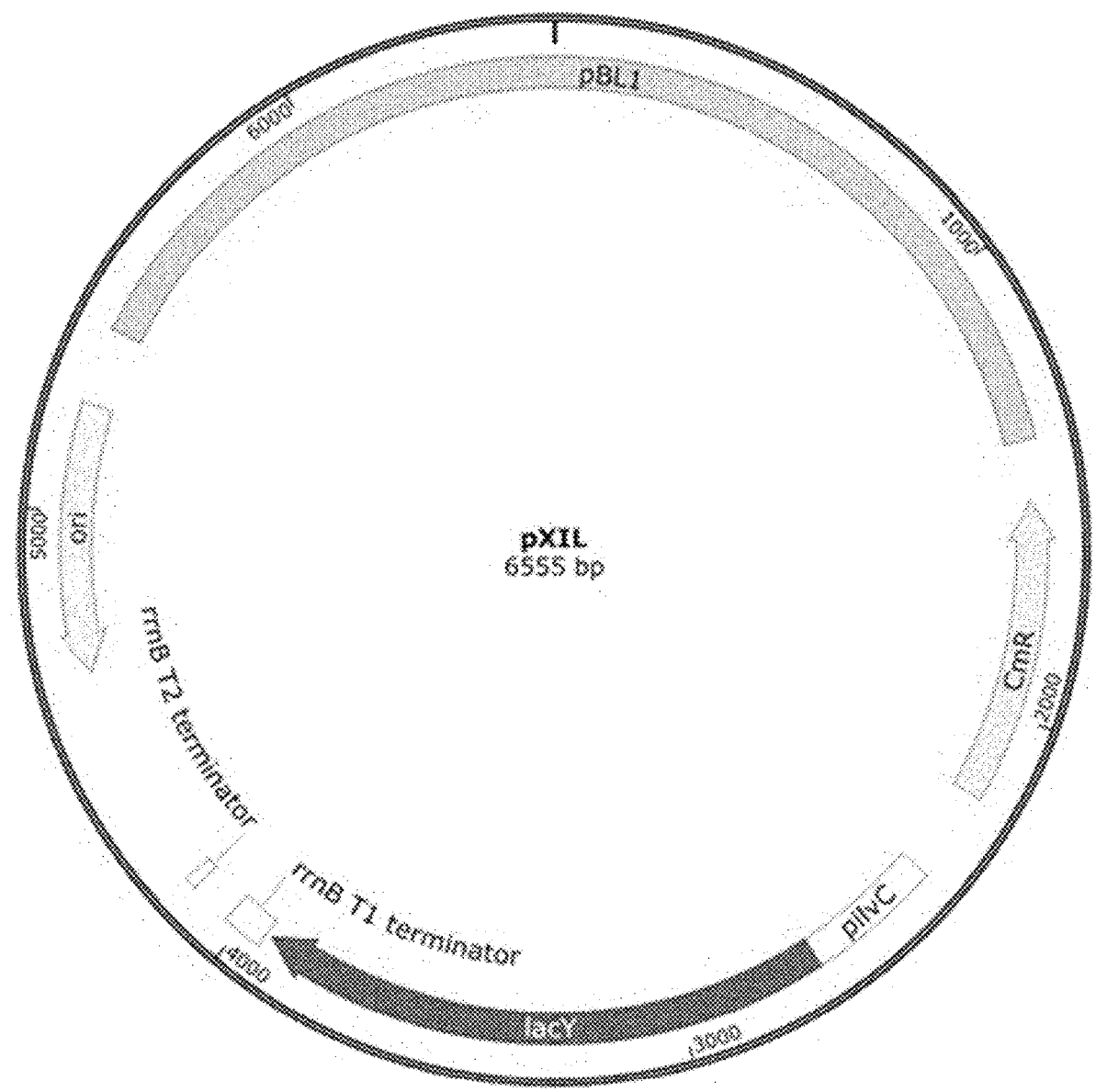
FIG. 2 a schematic diagram showing pXIL plasmids.

*Corynebacterium glutamicum* ATCC 13032 inserted with pFGW (Ps, FIG. 1) and pXIL (FIG. 2) was seed-cultured in a test tube containing 5 mL of BHI (brain heart infusion) medium supplemented with appropriate antibiotics (kanamycin 25 μg/mL and tetracycline 5 μg/mL) at 30° C. and 250 rpm for 12 hours. FIG. 1 is a schematic diagram showing a pFGW (Ps) plasmid, and FIG. 2 is a schematic diagram showing a pXIL plasmid.

Batch culture was carried out at 30° C. and at 250 rpm for 90 hours in a 250 mL flask containing 50 mL of minimum medium (($NH_4$)$_2SO_4$ 20 g/L, Urea 5 g/L, $KH_2PO_4$ 1 g/L, $K_2HPO_4$ 1 g/L, $MgSO_4 \cdot 7H_2O$ 0.25 g/L, MOPS 42 g/L, $CaCl_2$ 10 mg/L, Biotin 0.2 mg/L, Protocatechuic acid 30 mg/L, $FeSO_4 \cdot 7H_2O$ 10 mg/L, $MnSO_4 \cdot H_2O$ 10 mg/L, $ZnSO_4 \cdot 7H_2O$ 1 mg/L, $CuSO_4$ 0.2 mg/L, $NiCl_2 \cdot 6H_2O$ 0.02 mg/L, Glucose 40 g/L, Lactose 10 g/L, pH 7.0).

Figure 3:
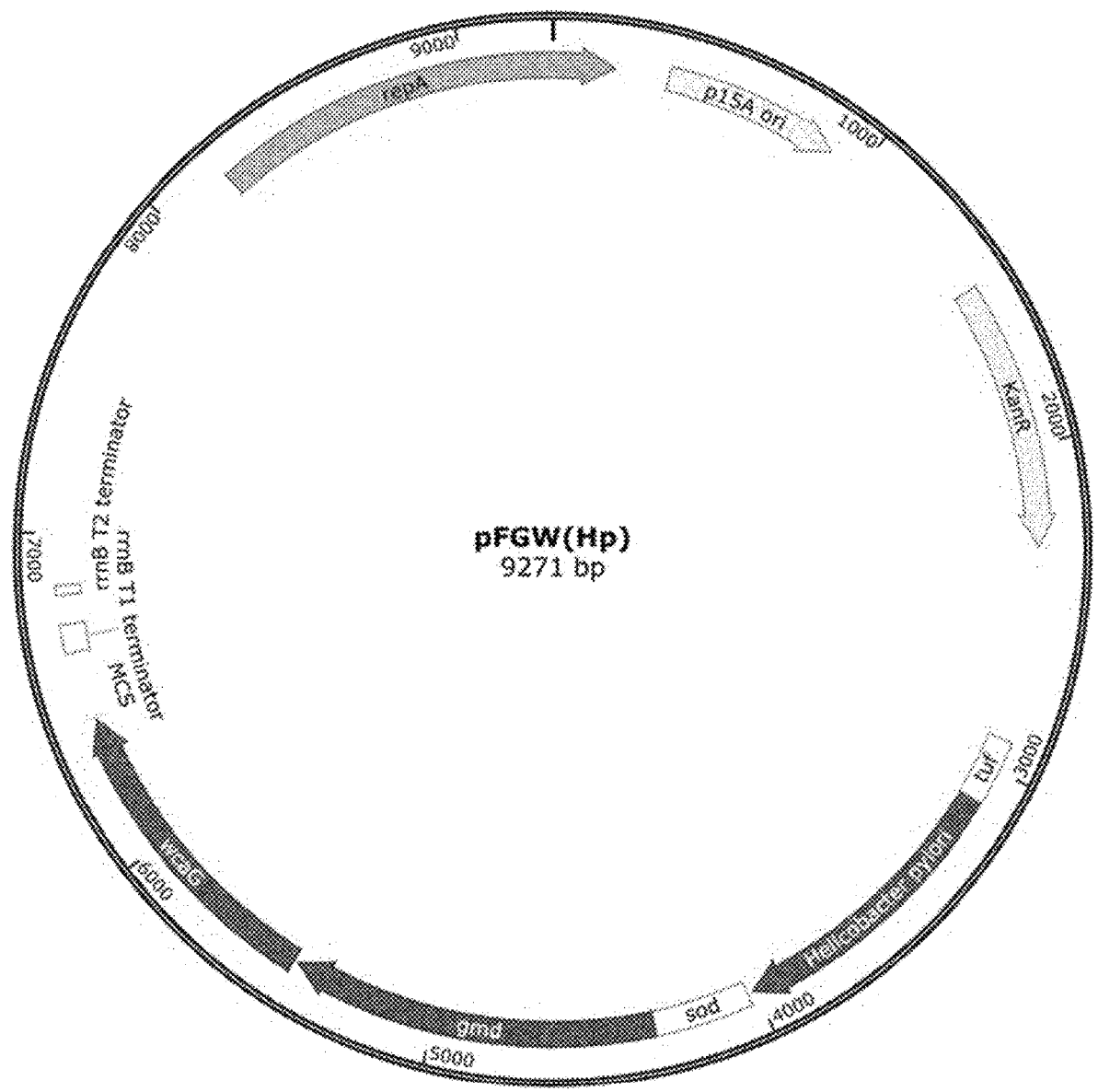
FIG. 3 a schematic diagram showing pFGW(Hp) plasmids.

Comparative Example 1: Culture of Recombinant Strain Introduced with *Helicobacter pylori*-Derived Fucosyltransferase The same culture method was used in Example 1 except that pFGW (Ps, FIG. 1) was changed to pFGW (Hp, FIG. 3). FIG. 3 is a schematic diagram showing a pFGW (Hp) plasmid.

Experimental Example 1: Comparison of 2'-FL Production of Recombinant Strains of Example 1 and Comparative Example 1

Figure 4:
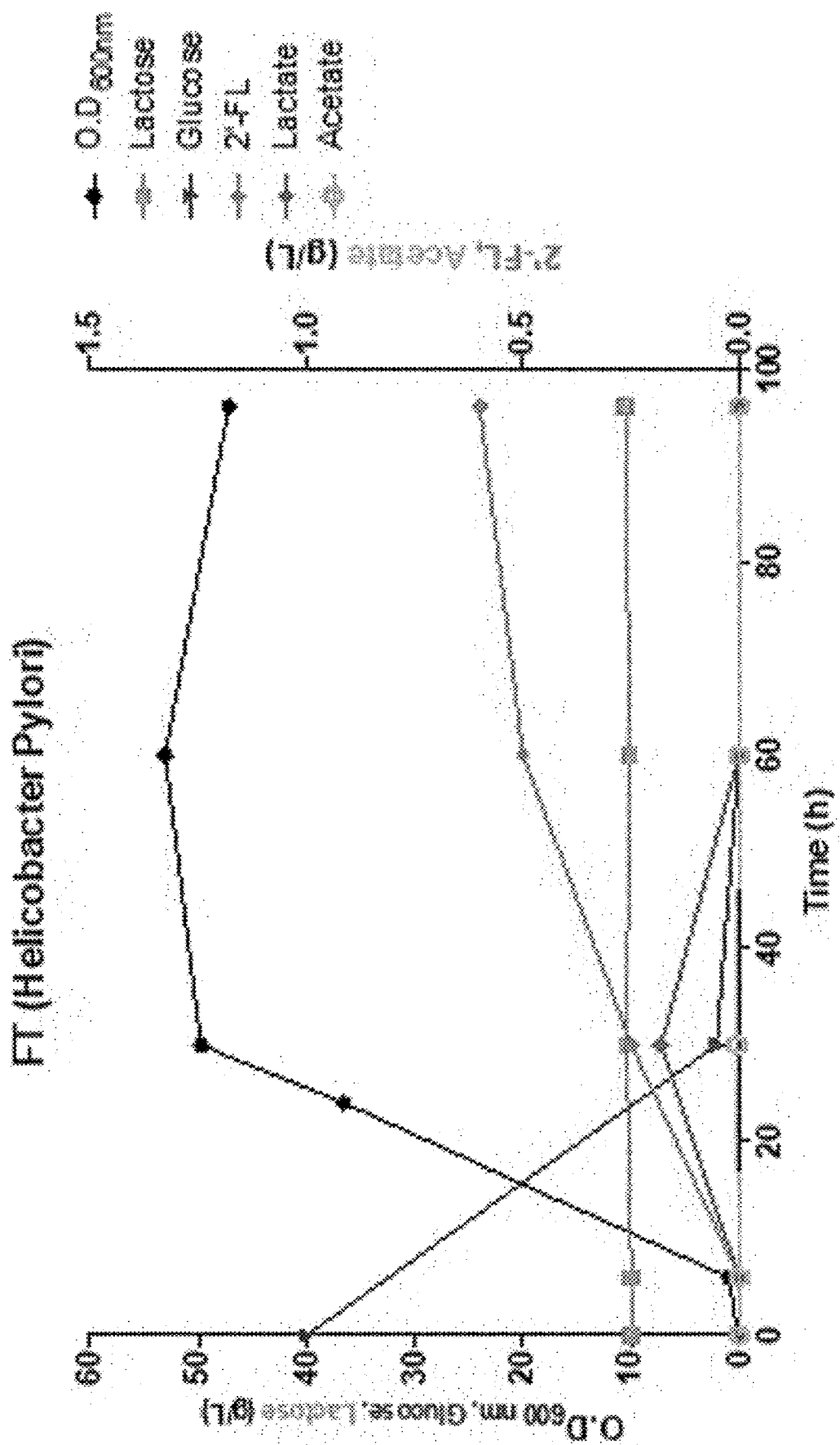
FIG. 4 shows the result of culture of a recombinant strain introduced with fucosyltransferase derived from *Helicobacter pylori* (●: Dried cell weight, ■: Lactose, ▼: Glucose, ◆: 2'-FL, ◇: Lactate, and ○: Acetate)
Figure 5:
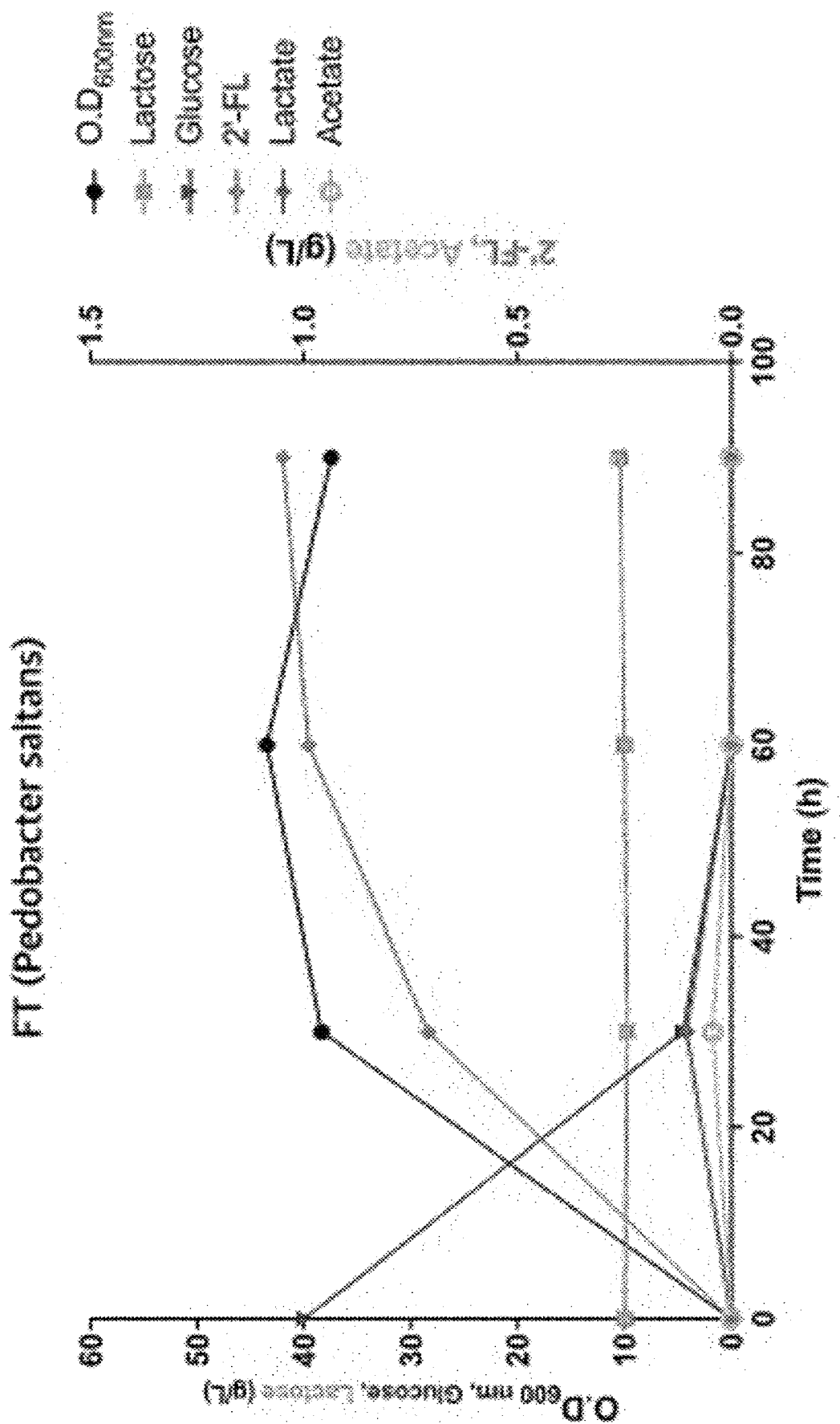
FIG. 5 shows the result of culture of a recombinant strain introduced with fucosyltransferase derived from *Pseudopedobacter saltans* (●: Dried cell weight, ■: Lactose, ▼: Glucose, ◆: 2'-FL, ◇: Lactate, and ○: Acetate).

The production amounts of 2'-FL in the recombinant strains prepared in Example 1 and Comparative Example 1 were compared (FIG. 4, FIG. 5, Table 5). FIG. 4 shows the result of culture of the recombinant strain introduced with fucosyltransferase derived from *Helicobacter pylori* and FIG. 5 shows the result of culture of the recombinant strain introduced with fucosyltransferase derived from *Pseudopedobacter saltans* (●: Dried cell weight, ■: Lactose, ▼: Glucose, ◆: 2'-FL, ◇ Lactate, and ○: Acetate).

TABLE 5

| Derived from fucosyllactose Transferase | Final dried cell weight (g/L) | Maximum 2'-FL concentration (mg/L) | 2'-FL/dried cell (mg/g) | Productivity (mg/L/h) |
|---|---|---|---|---|
| Helicobacter pylori | 15.51 | 600 | 38.68 | 6.25 |
| Pseudopedobacter saltans | 12.37 | 1,050 | 84.88 | 11.7 |

The experimental results showed that the recombinant strain introduced with fucosyltransferase derived from *Pseudopedobacter saltans* exhibited about twice the 2'-fucosyllactose productivity as the recombinant strain introduced with fucosyltransferase derived from *Helicobacter pylori*.

The invention claimed is:

1. A recombinant *Corynebacterium* sp. microorganism, which is transformed to express GDP-D-mannose-4,6-dehydratase, GDP-L-fucose synthase, lactose permease, and α-1,2-fucosyltransferase having an amino add sequence set forth in SEQ. ID NO: 5 derived from *Pseudopedobacter saltans*, wherein the recombinant *Corynebacterium* sp, Microorganism further expresses phosphomannomutase and GTP-mannose-1-phosphate guanylyltransferase.

2. The recombinant *Corynebacterium* sp. microorganism according to claim 1, wherein the recombinant *Corynebacterium* sp. microorganism selected from the group consisting of *Corynebacterium glutamicum*, *Corynebacterium ammoniagenes* and *Corynebacterium thermoaminogenes*.

3. The recombinant *Corynebacterium* sp. microorganism according to claim 1, wherein the α-1,2-fucosyltransferase having an amino acid sequence set forth in SEQ ID NO: 5 is encoded by a nucleic acid sequence set forth in SEQ ID NO: 4.

4. The recombinant *Corynebacterium* sp. microorganism according to claim 1, wherein the recombinant *Corynebacterium* sp. microorganism is transformed to overexpress phosphomannomutase and is transformed to overexpress GTP-mannose-1-phosphate guanylyltransferase.

5. A method of producing 2'-fucosyllactose comprising culturing, the recombinant *Corynebacterium* sp. microorganism according to claim 1, in a medium supplemented with lactose.

6. The method according to claim 5, wherein the medium further comprises glucose.

* * * * *